United States Patent [19]

Braun et al.

[11] Patent Number: 5,481,029
[45] Date of Patent: Jan. 2, 1996

[54] PROCESS FOR PREPARATION OF KETONES

[75] Inventors: Max Braun, Wedemark; Johannes Eicher, Garbsen; Werner Rudolph, Hannover; Kerstin Eichholz, Langenhagen, all of Germany

[73] Assignee: Solvay Fluor und Derivate GmbH, Hannover, Germany

[21] Appl. No.: 233,622

[22] Filed: Apr. 26, 1994

[30] Foreign Application Priority Data

Apr. 27, 1993 [DE] Germany .................. 43 13 794.6
Jun. 24, 1993 [DE] Germany .................. 43 21 017.1

[51] Int. Cl.$^6$ .................................................. C07C 67/10
[52] U.S. Cl. .................. 560/234; 568/394; 568/346; 568/314
[58] Field of Search .................. 568/388, 394, 568/346, 341, 314; 560/234, 224; 562/577

[56] References Cited

U.S. PATENT DOCUMENTS

| | | | |
|---|---|---|---|
| 2,369,250 | 2/1945 | Reeder et al. | 568/388 |
| 4,276,225 | 6/1981 | Lantzsch et al. | 568/346 |
| 5,093,532 | 3/1992 | Baasner et al. | 568/401 |
| 5,210,272 | 5/1993 | Palmer | 568/397 |
| 5,274,136 | 12/1993 | Mills et al. | 568/388 |

FOREIGN PATENT DOCUMENTS 4025188  2/1992  Germany .................. 568/388

OTHER PUBLICATIONS

Hudson et al., J. A. C. S., 63:3163–4 (1941).
Henne et al., J. A. C. S., 69:1819–20 (1947).
*Chemical Abstracts*, 107:197496y (1987).
*Japanese High Technology Monitor*, vol. 10, no. 2, p. 3, Entry No. 31607 (1987).
Kal'fa et al., "New method for . . . ", *J. Fluorine Chem.*, 58:358 (1992) P90.

*Primary Examiner*—James H. Reamer
*Attorney, Agent, or Firm*—Evenson, McKeown, Edwards & Lenahan

[57] ABSTRACT

A process for preparing ketones, for example $CF_3C(O)CH_3$, $CF_3C(O)CH_2C(O)CF_3$ and $CF_3C(O)CF_2H$, in which β-ketoesters are transesterified and decarboxylated using a carboxylic acid, for example trifluoroacetic acid, in the presence of a catalyst, particularly an "onium" salt of a carboxylic acid or an effective amount of a proton-donating acid, preferably a sulfonic acid such as alkyl- or arylsulfonic acids, or a mineral acid. The process is advantageously carried out in the absence of water, so that no formation of acetals or hydrates occurs, and no dehydrating step is needed. The process is simple to carry out, and if transesterification is carried out with a sufficiently active carboxylic acid, for example with trifluoroacetic acid, the presence of an additional catalyst is unnecessary.

21 Claims, No Drawings

PROCESS FOR PREPARATION OF KETONES

BACKGROUND OF THE INVENTION

The invention relates to a process for preparing ketones.

Ketones are useful intermediates in chemical synthesis. 1,1,1-Trifluoroacetone, for example, is an important intermediate in the preparation of biologically active intermediate compounds, see U.S. Pat. No. 5,093,532. This document describes the preparation of halomethyl ketones from the respective halomethylnitro compound by reaction with alkoxide and subsequent ozonization. The product is obtained as hydrate, acetal or hemiacetal. This patent also describes further processes for preparing ketones, which proceed via Grignard compounds (this type of reaction requires increased safety precautions and, in addition, unwanted waste products are produced) or which involve the acid-catalyzed cleavage of ketoesters. In the latter process, hydrates of the ketones are likewise obtained. Furthermore, deacylation is often observed instead of the desired decarboxylation. Other processes provide for catalysis by transition metals; ketones having a $CF_3$ group could be complexed by metals.

Despite the various processes known in the prior art, there remains a need for better ways to prepare ketones.

SUMMARY OF THE INVENTION

Accordingly, it is the object of the present invention to provide a new process for preparing ketones.

Another object of the invention is to provide a process in which anhydrous ketones are directly obtained without dehydration.

A further object of the invention is to provide a process for preparing ketones which is simple to carry out industrially.

A still further object of the invention is to provide a process for preparing ketones which can also be used to prepare certain esters.

These and other objects are achieved in accordance with the invention by providing a process for preparing a ketone from a ketoester compound, comprising transesterifying the ketoester compound with a carboxylic acid to obtain a liberated ketoacid, and decarboxylating the liberated ketoacid to obtain a corresponding ketone.

DETAILED DESCRIPTION OF PREFERRED EMBODIMENTS

The process of the invention for preparing ketones from ketoester compounds provides for transesterification of the ketoester compound with a carboxylic acid and decarboxylation of the liberated acid to obtain the ketone. As used herein the term "liberated acid" refers to a carboxylic acid, containing at least one keto group, which corresponds to the ketoester compound used. β-Ketoesters are preferred.

Unlike known processes, a transesterifiction occurs in the process of the invention; it is therefore preferably carried out without addition of water (for example without addition of aqueous acid solutions). It is particularly preferably carried out in the absence of water. However, satisfactory results can also be achieved if small amounts of water which at most inconsequentially impair the desired outcome, for example up to 3% by weight or less, are present in the reaction mixture. If desired, water-binding agents can be added. One water-binding agent, which additionally has a catalytic effect, is sulfuric acid.

The reaction (transesterification and decarboxylation) occurs spontaneously between many carboxylic acids and ketoester compounds at an at least satisfactory rate; if desired, the reaction can be accelerated by heating the reaction mixture. It has been found that carboxylic acids having a higher acid strength are more reactive. Whether the reaction of a certain carboxylic acid with a certain ketoester compound proceeds at a satisfactory rate can easily be checked by those skilled in the art by mixing the two components and slowly heating the mixture. The evolution of carbon dioxide gas indicates the reaction. Carboxylic acids activated by electron-attracting groups, for example carboxylic acids which are substituted in the α-position by halogens, react very well with ketoester compounds.

If it is found that the reaction of certain carboxylic acids with ketoester compounds proceeds at an undesirably slow rate, the reaction can be catalyzed. Suitable compounds for this purpose are those having a greater acid strength than the carboxylic acid used, for example more acidic carboxylic acids such as trifluoroacetic acid, mineral acids such as sulfuric acid or phosphoric acid, sulfonic acids or else "onium" salts of carboxylic acids. Such catalysis can, of course, also be provided for those reactions which proceed at a satisfactory rate even without additional catalyst, as is the case, for example, with trifluoroacetic acid as the carboxylic acid used.

The ketones which are preferably prepared according to the invention are those of the general formula (I)

$$R^1C(O)CH_nR^2{}_{3-n} \qquad (I)$$

in which $R^1$ is alkyl having from 1 to 10 carbon atoms; alkyl substituted by at least 1 halogen atom and having from 1 to 10 carbon atoms; aryl; aryl substituted by at least 1 halogen atom; arylalkyl; $R^2$ is hydrogen; alkyl having from 1 to 10 carbon atoms; C1— to C10-alkyl substituted by at least one halogen atom; aryl; aryl substituted by at least 1 halogen atom; arylalkyl; halogen or $C(O)R^3$, in which $R^3$ is alkyl having from 1 to 10 carbon atoms; alkyl substituted by at least 1 halogen atom and having from 1 to 10 carbon atoms; aryl; aryl substituted by at least one halogen atom; or arylalkyl, and n=1 or 2, by reaction of a carboxylic acid having from 1 to 10 carbon atoms or a carboxylic acid substituted by at least 1 halogen atom and having from 1 to 10 carbon atoms with a ketoester compound in the form of a carboxylate or dicarboxylate compound of the general formula (II)

$$R^1C(O)CR^2{}_{3-n}[C(O)OR^4]_n \qquad (II)$$

in which n, $R^1$ and $R^2$ have the meanings given above; $R^4$ is alkyl having from 1 to 10 carbon atoms; alkyl substituted by at least 1 halogen atom and having from 1 to 10 carbon atoms; aryl; aryl substituted by at least 1 halogen atom; or arylalkyl.

A preferred variant provides for the use of a catalyst, by carrying out the decarboxylation under transesterification with a carboxylic acid in the presence of a reaction-catalyzing amount of an "onium" salt of a carboxylic acid and/or of a concentrated acid selected from the group comprising mineral acids, aryl-sulfonic acids and alkylsulfonic acids.

As used herein, the term "onium" refers to cations having positively charged nitrogen, for example protonated aromatic nitrogen bases such as pyridinium or protonated alkyl-, dialkyl- or trialkyl-ammonium cations having up to 20 carbon atoms, or refers to cycloalkyl-substituted ammonium compounds or cycloaliphatic nitrogen bases such as piperidinium. The term "mineral acids" includes oxo acids of elements of Groups IV to VII of the periodic table of elements, in particular phosphoric acid, sulfuric acid, fluorosulfuric acid, and chlorosulfuric acid. The term "alkylsulfonic acids" includes $C_1$–$C_5$-alkylsulfonic acids in which the alkyl group may be substituted by 1 or more halogen atoms, for example methanesulfonic acid and trifluoromethanesulfonic acid. The term "arylsulfonic acids" includes phenylsulfonic acid and sulfonic acids having a phenyl group which may be substituted by 1 or more halogen atoms and/or by 1 or more $C_1$–$C_2$-alkyl groups, for example p-toluenesulfonic acid. The amount of carboxylic acid to be used is advantageously at least 0.8 mole per mole of carboxyl group to be transesterified. The reaction is preferably carried out in the absence of water.

If n=1, the ketones correspond to the formula $R^1C(O)CHR^2_2$. The two substituents $R^2$ can in this case be identical or different. If n=2, the starting materials are dicarboxylate compounds corresponding to the formula $R^1C(O)CR^2[C(O)OR^4]_2$. The substituents $R^2$ can in this case be identical or different.

In a very particularly preferred embodiment of the invention, the reaction is carried out under decarboxylation in the presence of a transesterification-catalyzing amount of an "onium" salt of a carboxylic acid having from 1 to 10 carbon atoms, of a metal or "onium" salt of a carboxylic acid substituted by at least 1 halogen atom and having from 1 to 10 carbon atoms, of a concentrated mineral acid, of an arylsulfonic acid, or of an alkylsulfonic acid.

If a carboxylic acid is used in the presence of an "onium" salt of a carboxylic acid, then these can be different carboxylic acids or preferably the same carboxylic acid.

The mineral acid used is preferably sulfuric acid, which is particularly suitable.

Exceptionally suitable carboxylic acid salts include "onium" salts, where "onium" represents cations having positively charged nitrogen, preferably a nitrogen-containing cation corresponding to the formula $R'R''R'''R^{IV}N^+$, where $R'$, $R''$, $R'''$ and $R^{IV}$ are independently selected from hydrogen, alkyl having from 1 to 20 carbon atoms, or aralkyl, or where $R'$ and $R''$ or where $R'''$ and $R^{IV}$, or where $R'$, $R''$ and $R'''$ or where $R'$, $R''$, $R'''$ and $R^{IV}$ form, optionally with inclusion of the nitrogen atom, saturated or unsaturated ring systems. "Onium" salts in which the "onium" is ammonium, pyridinium or $R^{1'}R^{2'}R^{3'}R^{4'}N^+$, where $R^{1'}$, $R^{2'}$, $R^{3'}$ and $R^{4'}$ are, independently of one another, hydrogen, alkyl having from 1 to 15 carbon atoms, aryl or benzyl, are particularly suitable. "Aryl" here is, in particular, phenyl or phenyl substituted by 1 or more $C_1$–$C_2$-alkyl groups. Examples of such cations which may be mentioned include pyridinium, anilinium, piperidinium, benzyltriethylammonium and triethylammonium.

The carboxylic acid used in the process of the invention is preferably a carboxylic acid of the formula (III), $R^1COOH$, where $R^1$ has the meaning given above. $R^1$ is preferably alkyl substituted by from 1 to 5 halogen atoms and having 1 or 2 carbon atoms, in particular $CH_2F$, $CHF_2$ or $CF_3$. $R^2$ is preferably hydrogen, fluorine or $C(O)R^3$, where $R^3$ is $CH_3$, $CH_2F$, $CHF_2$ or $CF_3$.

In one preferred embodiment, $R^4$ is alkyl which optionally may be substituted by 1 or more halogen atoms and which contains from 1 to 6 carbon atoms, preferably from 1 to 3 carbon atoms, in particular methyl, ethyl, propyl, 1,1,1-trifluoroethyl or pentafluoropropyl.

In another embodiment of the invention n is 1. Ketones of the formula $R^1C(O)CHR^2_2$ are then prepared from $R^1C(O)CR^2_2COOR^4$. For example, $CF_3C(O)CH_3$ can be prepared from $CF_3C(O)CH_2COOMe$, $CF_3C(O)CH_2COOEt$ or $CF_3C(O)CH_2COOCH_2CF_3$. $CF_3C(O)CH_2F$ or $CH_2FC(O)CH_2F$ and other ketones can be prepared analogously.

In yet another embodiment n is 2. Ketones of the formula $R^1C(O)CH_2R^2$ are then prepared starting from dicarboxylates of the formula $R^1C(O)CR^2[C(O)OR^4]_2$.

Diketo compounds are prepared starting from ketoesters of the formula $R^1C(O)CR^2[C(O)R^3][C(O)OR^4]$ or $R^1C(O)C[C(O)R^3][C(O)OR^4]_2$.

The amount of carboxylic acid is advantageously selected so that at least 0.8 mole of carboxylic acid is used per mole of ester group in the compound of formula (II). Advantageously, the molar ratio of carboxylic acid to ester groups in the compound of formula (II) lies between 0.9:1 and 1.1:1.

The temperature at which the process is carried out advantageously lies in the range from 70° to 130° C. The pressure advantageously lies in the range from 0.01 bar (absolute) to 2 bar (absolute).

The "onium" salt of the carboxylic acid or the mineral acid is advantageously present in a concentration from 50 to 900 g/l in the reaction mixture.

In another preferred embodiment, the carboxylic acid used is the particularly strong acid trifluoroacetic acid and no additional catalyst is used. This embodiment of the process of the invention for preparing ketones by decarboxylation of ketoester compounds is thus characterized by the decarboxylation being carried out under transesterification with trifluoroacetic acid.

Catalysts such as "onium" salts of carboxylic acids or acids such as mineral acids, arylsulfonic acids and alkylsulfonic acids are not necessary in the transesterification with trifluoroacetic acid. The amount of trifluoroacetic acid used is advantageously at least 0.8 mole per mole of carboxyl group to be transesterified. This variant is also preferably carried out without addition of water, in particular in the absence of water and using the ester to be decarboxylated as starting material and solvent.

The amount of trifluoroacetic acid is advantageously chosen so that at least 0.8 mole of trifluoroacetic acid is used per mole of ester group in the compound of formula (II). Advantageously, the molar ratio of trifluoroacetic acid to ester groups in the compound of formula (II) lies between 0.9:1 and 1.1:1.

Here too, the temperature at which the process is carried out is advantageously at least 70° C., preferably in the range from 100° to 130° C. The pressure advantageously lies in the range from 0.01 bar (absolute) to 2 bar (absolute).

If desired, the process of the invention can be carried out in the presence of an inert solvent, for example in the presence of hydrocarbons or perhalogenated compounds. If liquid, the mineral acid, the carboxylic acid or the ketoester used can also serve as a solvent. Even very small amounts of mineral acids have a catalytic action. Thus, amounts as small as 1% by weight or less are sufficient. Advantageously, 5% by weight or more are added.

The ketoester compounds serving as starting compounds are known or can be prepared by or analogously to standard methods. As can be seen from the foregoing observations, the process of the invention can also be used to prepare β-diketo compounds. For this purpose, the starting compounds are, for example, compounds corresponding to the formula (IV)a, $R^1C(O)CH_2C(O)OR^4$ or (IV)b, $R^1C(O)CH[C(O)OR^4]_2$, or (IV)c, $R^1C(O)CHR^2C(O)OR^4$ (wherein $R^1$, $R^2$ and $R^4$ have the abovedescribed meanings). To prepare these compounds, the proton can be replaced by a $R^3(CO)$ group. For this purpose, for example, the compound of the formula (IV) can be reacted with $R^3C(O)Cl$ in the presence of a base, for example triethylamine. For example, $CH_2(COOEt)_2$ can be reacted with $CF_3C(O)Cl$ and $Et_3N$ to give $CF_3C(O)CH(COOEt)_2$. The decarboxylation of the ketodiester by means of, for example, trifluoroacetic acid, optionally in the presence of sulfuric acid, gives $CF_3C(O)CH_3$. Analogously, the compound $CF_3C(O)CH_2C(O)CH_3$ is formed from $CH_3C(O)CH_2COOEt$ after trifluoroacetylation and decarboxylation. These and similar diketones are complexing agents and can be used, for example, in metal recycling.

Other ketoester compounds can also be produced in an analogous way by acylation of esters or diesters.

The process of the invention can also be operated continuously. For this purpose, carboxylic acid and ketoester compound are fed into the reaction mixture, and the resulting ketone, optionally also the resulting ester, is or are removed, for example by distillation.

The present invention also has a further aspect, in addition to ketone preparation. The transesterification of the carboxylic acid forms an ester of this carboxylic acid, which can be isolated from the reaction mixture. Use of certain carboxylic acids and of ketoester compounds having certain ester groups makes possible the specific synthesis of certain esters, for example of trifluoroacetic acid, which might be preparable only with difficulty by other methods.

The process of the invention facilitates the industrially simple preparation of keto compounds which are obtained in anhydrous form. In addition, specific production of esters is also possible. The separation of the reaction mixtures can be carried out by distillation.

The following examples illustrate the invention in further detail without restricting its scope.

Example 1: Preparation of the diethyl 1,1,1-trifluoro-2-oxo-propane-3, 3-dicarboxylate required as starting material for the decarboxylation, by reaction of trifluoroacetyl chloride with diethyl malonate and triethylamine.

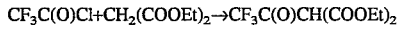

$CF_3C(O)Cl + CH_2(COOEt)_2 \rightarrow CF_3C(O)CH(COOEt)_2$

The preparation is carried out analogously to the method described by A. F. Ermolov, A. F. Eleev, A. F. Benda and G. A. Sokol'skii in *Zh. Org. Khim.* 23(1) (1987), pages 105–112. For this purpose, approximately equimolar amounts of the starting compounds are reacted in diethyl ether with two equivalents of triethylamine. The $[CF_3C(O)C(COOEt)_2]^- HNEt_3^+$ formed was converted into diethyl 1,1,1-trifluoro-2-oxopropane-3, 3-dicarboxylate by addition of sulfuric acid. This compound was then extracted from the reaction mixture with diethyl ether and purified by distillation.

Example 2: Preparation of 1,1,1-trifluoroacetone from diethyl 1,1,1-trifluoro-2-oxopropane-3,3-dicarboxylate by transesterification with trifluoroacetic acid/pyridinium trifluoroacetate and subsequent decarboxylation.

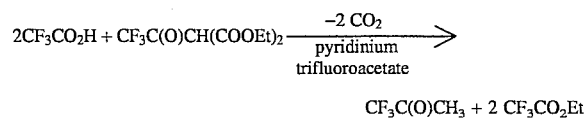

$2CF_3CO_2H + CF_3C(O)CH(COOEt)_2 \xrightarrow[\text{pyridinium trifluoroacetate}]{-2CO_2}$ $CF_3C(O)CH_3 + 2 CF_3CO_2Et$ A glass apparatus fitted with a 20 cm Vigreux column having two downstream cold traps cooled to −78° C. and with a KPG stirrer was charged with 35.9 g (0.45 mole) of pyridine, and 149.2 g (1.30 mole) of trifluoroacetic acid were added dropwise with light cooling at from 50° to 70° C. After the addition of 51.2 g (0.20 mole) of diethyl 1,1,1-trifluoro-2-oxopropane-3, 3-dicarboxylate, the reaction mixture was heated in an oil bath to from 120° to 140° C., the decarboxylation commencing at 90° C. After a reaction time of 10 hours, the yield of 1,1,1-trifluoroacetone in admixture with ethyl trifluoroacetate was 72.6% of theoretical.

Example 3: Preparation of 1,1,1-trifluoroacetone from ethyl ω,ω,ω-trifluoroacetoacetate by transesterification with trifluoroacetic acid in concentrated sulfuric acid and decarboxylation at from 90° to 120° C.

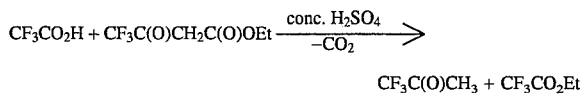

$CF_3CO_2H + CF_3C(O)CH_2C(O)OEt \xrightarrow[-CO_2]{\text{conc. } H_2SO_4}$ $CF_3C(O)CH_3 + CF_3CO_2Et$ A glass apparatus fitted with a 20 cm Vigreux column having two downstream cold traps cooled to −78° C. and with a KPG stirrer was charged with 100 ml of concentrated $H_2SO_4$ (also serves as solvent) and 109.5 g (0.96 mole) of trifluoroacetic acid at room temperature. After addition of 58.9 g (0.32 mole) of ethyl ω,ω,ω-tri-fluoroacetoacetate, the reaction mixture was heated while stirring in an oil bath to temperatures from 90° to 120° C. internal temperature, the decarboxylation commencing at about 75° C. At the beginning of the reaction the excess trifluoroacetic acid was partially distilled off. The yield of 1,1,1-trifluoroacetone was, after a reaction time of 7 hours, 86% of theoretical as a mixture with ethyl trifluoroacetate, the oil bath temperature being raised to 160° C. to finally drive off the ethyl trifluoroacetate and remaining trifluoroacetic acid. Subsequent distillation via a packed column gave pure trifluoroacetone.

Example 4: Preparation of 1,1,1-trifluoroacetone from diethyl 1,1,1-trifluoro-2-oxopropane-3,3-dicarboxylate by transesterification with trifluoroacetic acid/methanesulfonic acid and subsequent decarboxylation at from 130° to 160° C.

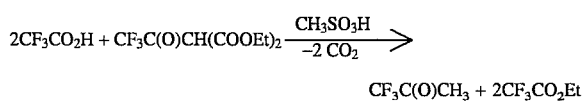

$2CF_3CO_2H + CF_3C(O)CH(COOEt)_2 \xrightarrow[-2CO_2]{CH_3SO_3H}$ $CF_3C(O)CH_3 + 2CF_3CO_2Et$ A glass apparatus fitted with a 20 cm Vigreux column having two downstream cold traps cooled to −78° C. and with a KPG stirrer was charged with 148.24 g (1.54 mole) of methanesulfonic acid and 68.41 g (0.60 mole) of trifluoroacetic acid at room temperature. After the addition of 51.24 g (0.20 mole) of diethyl 1,1,1-trifluoro-2-oxopropane-3, 3-dicarboxylate, the reaction mixture was heated while stirring (600 rpm) in an oil bath to temperatures from 130° to 160° C. internal temperature, the decarboxylation commencing at about 90° C. At the beginning of the reaction the excess trifluoroacetic acid was partially distilled off. The yield of 1,1,1-trifluoroacetone was, after a reaction time of 9 hours, 79% of theoretical as a mixture with ethyl trifluoroacetate, with the oil bath temperature being raised to 200° C. to finally drive off the ethyl trifluoroacetate and the excess trifluoroacetic acid.

Example 5: Preparation of 1,1,1-trifluoroacetone from diethyl 1,1,1-trifluoro-2-oxopropane-3,3-dicarboxylate by transesterification with trifluoroacetic acid in concentrated sulfuric acid and decarboxylation at from 90° to 120° C.

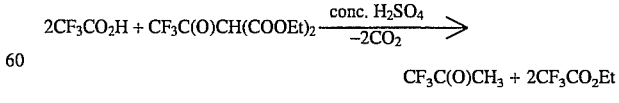

$2CF_3CO_2H + CF_3C(O)CH(COOEt)_2 \xrightarrow[-2CO_2]{\text{conc. } H_2SO_4}$ $CF_3C(O)CH_3 + 2CF_3CO_2Et$ A glass apparatus fitted with a 20 cm Vigreux column having two downstream cold traps cooled to −78° C. and with a KPG stirrer was charged with 100 ml of concentrated $H_2SO_4$ and 68.41 g (0.60 mole) of trifluoroacetic acid at room temperature. After the addition of 51.24 g (0.20 mole) of diethyl 1,1,1-trifluoro-2-oxopropane-3,3-dicarboxylate, the reaction mixture was heated while stirring (600 rpm) in an oil bath to temperatures from 90° to 120° C. internal temperature, the decarboxylation commencing at about 90° C. At the beginning of the reaction the excess trifluoroacetic acid was partially distilled off. After a reaction time of 7 hours, with the oil bath temperature being raised to 160° C. to finally drive off the ethyl trifluoroacetate and remaining trifluoroacetic acid, the yield of 1,1,1-trifluoroacetone as a mixture with ethyl trifluoroacetate was 82% of theoretical.

A sulfuric acid/sulfolane mixture (30 ml of concentrated sulfuric acid/70 ml of sulfolane) was also tested and gave approximately the same results. It was possible to carry out a plurality of successive decarboxylations using the same catalyst mixture without problems. Use of chlorosulfuric and fluorosulfuric acid as catalyst component resulted in the formation of unidentified by-products. If too much trifluoroacetic acid is removed at the beginning of the reaction, the decarboxylation occurs with the formation of ethylene.

The separation of the trifluoroacetone/ethyl trifluoroacetate mixture obtained from all the reactions is carried out subsequently by distillation via a 40 cm packed column.

Example 6: Continuous preparation of 1,1,1-trifluoroacetone in a sustained run.

Example 3 was repeated. An amount of starting material corresponding to the amount of 1,1,1-trifluoroacetone and ethyl trifluoroacetate distilled out of the reaction mixture was fed continuously into the glass apparatus. The yield of 1,1,1-trifluoroacetone after a run of 15 days was 95% of theoretical.

Example 7: Process for continuously preparing 1,1,1-trifluoroacetone by transesterification of ethyl ω,ω,ω-trifluoroacetoacetate with trifluoroacetic acid under decarboxylating conditions without addition of a catalytic mineral acid.

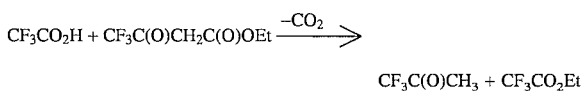

A 250 ml three-neck flask fitted with mechanical stirrer, 20 cm Vigreux column and two downstream cold traps cooled to −78° C. was charged with 149.5 g (0.81 mole) of ethyl trifluoroacetoacetate and 30.8 g (0.27 mole) of trifluoroacetic acid. The mixture was heated in an oil bath to 120° C., the decarboxylation commencing at 70° C. Continuous operation was achieved by keeping the level in the vessel constant and by dropwise addition of an equimolar mixture of the two reaction components. During a reaction time of 17.2 hours, a total of 1.08 moles of ethyl trifluoroacetate was converted to trifluoroacetone. The total yield of trifluoroacetone was 96.9%, that of ethyl trifluoroacetate was 99%. The separation of the ethyl trifluoroacetate/trifluoroacetone mixture was carried out by distillation via a 40 cm packed column.

Example 8: Process for continuously preparing 1,1,1-trifluoroactone by transesterification of ethyl ω,ω,ω-trifluoroacetoacetate with trifluoroacetic acid under decarboxylating conditions using ethyl ω,ω,ω-trifluoroacetoacetate as reaction component ($H_2SO_4$ catalysis with reduced amount of $H_2SO_4$).

151.0 g (0.82 mole) of ethyl trifluoroacetoacetate and 30.8 g (0.27 mole) of trifluoroacetic acid were charged into a 250 ml three-neck flask fitted with a KPG stirrer, 20 cm Vigreux column and two downstream cold traps cooled to −78° C., and were admixed with 20 ml of concentrated $H_2SO_4$. The mixture was heated to 110° C. (bottom temperature) in an oil bath, the decarboxylation slowly commencing at 75° C. Continuous operation was achieved by keeping the level in the vessel constant, by dropwise addition of an equimolar mixture of the two reaction components. In this manner, 159 mmole of ethyl trifluoroacetoacetate/trifluoroacetic acid mixture were converted every hour into trifluoroacetone and ethyl trifluoroacetate. The total yield of trifluoroacetone isolated was 92.9%, that of ethyl trifluoroacetate was 99% (as mixture). The separation of the mixture was carried out by distillation via a 40 cm packed column.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A process for preparing a ketone from a β-ketoester compound, comprising transesterifying the β-ketoester compound with a carboxylic acid to obtain a liberated ketoacid, and decarboxylating the liberated ketoacid to obtain a corresponding ketene.

2. A process according to claim 1, wherein the preparation of ketones of the general formula (I)

in which $R^1$ is alkyl having from 1 to 10 carbon atoms; alkyl substituted by at least 1 halogen atom and having from 1 to 10 carbon atoms; aryl; aryl substituted by at least 1 halogen atom; arylalkyl; $R^2$ is hydrogen; alkyl having from 1 to 10 carbon atoms;alkyl substituted by at least one halogen atom and having 1 to 10 C-atoms; aryl; aryl substituted by at least 1 halogen atom; arylalkyl; halogen or $C(O)R^3$, in which $R^3$ is alkyl having from 1 to 10 carbon atoms; alkyl substituted by at least 1 halogen atom and having from 1 to 10 carbon atoms; aryl; aryl substituted by at least 1 halogen atom; or arylalkyl, and n=1 or 2, is carried out by reaction of a carboxylic acid having from 1 to 10 carbon atoms or a carboxylic acid substituted by at least 1 halogen atom and having from 1 to 10 carbon atoms with a ketoester compound in the form of a carboxylate or dicarboxylate compound of the general formula (II)

in which n, $R^1$ and $R^2$ have the meanings given above; $R^4$ is alkyl having from 1 to 10 carbon atoms; alkyl substituted by at least 1 halogen atom and having from 1 to 10 carbon atoms; aryl; or aryl substituted by at least 1 halogen atom; or arylalkyl.

3. A process according to claim 1, wherein said carboxylic acid corresponds to formula

wherein $R^1$ is alkyl having from 1 to 10 carbon atoms; alkyl substituted by at least 1 halogen atom and having from 1 to 10 carbon atoms; aryl; aryl substituted by at least 1 halogen atom; or arylalkyl.

4. A process according to claim 3, wherein $R^1$ is alkyl substituted by from 1 to 5 halogen atoms and having 1 or 2 carbon atoms.

5. A process according to claim 4, wherein $R^1$ is $CH_2F$, $CHF_2$ or $CF_3$.

6. A process according to claim 2, wherein $R^2$ is hydrogen, fluorine or $C(O)R^3$ in which $R^3$ is $CH_3$, $CH_2F$, $CHF_2$ or $CF_3$.

7. A process according to claim 2, wherein $R^4$ is alkyl having from 1 to 6 carbon atoms or halogen-substituted alkyl having from 1 to 6 carbon atoms.

8. A process according to claim 7, wherein $R^4$ represents an alkyl group containing from 1 to 3 carbon atoms.

9. A process according to claim 7, wherein $R^4$ is methyl, ethyl, propyl, 1,1,1-trifluoroethyl or pentafluoropropyl.

10. A process according to claim 1, wherein the decarboxylation is carried out under transesterification with a carboxylic acid in the presence of a transesterification-catalyzing amount of at least one catalyst selected from the group consisting of "onium" salts of carboxylic acids and concentrated mineral acids, arylsulfonic acids and alkylsulfonic acids.

11. A process according to claim 10, wherein the decarboxylation is carried out under transesterification in the presence of a transesterification-catalyzing amount of a catalyst selected from the group consisting of "onium" salts of carboxylic acids having from 1 to 10 carbon atoms, metal or "onium" salts of carboxylic acids substituted by at least 1 halogen atom and having from 1 to 10 carbon atoms, concentrated mineral acids, arylsulfonic acids, alkylsulfonic acids, and carboxylic acids substituted by at least 1 halogen atom and having up to 4 carbon atoms.

12. A process according to claim 2, wherein the reaction of the compound of the formula (II) with the carboxylic acid is carried out in the presence of a transesterification-catalyzing amount of an "onium" salt of the same carboxylic acid or of a concentrated mineral acid selected from the group consisting of sulfuric acid and phosphoric acid, or of methanesulfonic acid.

13. A process according to claim 12, wherein an "onium" salt of the same carboxylic acid or sulfuric acid is used.

14. A process according to claim 1, wherein $CF_3C(O)CH_3$ is prepared by reacting trifluoroacetic acid with $CF_3C(O)CH_2COOEt$ or $CF_3C(O)CH(COOEt)_2$ in the presence of a transesterification-catalyzing amount of an "onium" salt of trifluoroacetic acid or concentrated sulfuric acid.

15. A process according to claim 1, wherein the "onium" salt of the carboxylic acid or the concentrated mineral acid is present in a concentration from 50 to 900 g/liter.

16. A process according to claim 1, wherein trifluoroacetic acid is used as the carboxylic acid and no additional catalyst is present.

17. A process according to claim 16, wherein $CF_3C(O)CH_3$ is prepared by reacting trifluoroacetic acid with $CF_3C(O)CH_2COOEt$ or $CF_3C(O)CH(COOEt)_2$.

18. A process according to claim 17, wherein from 0.9 to 1.1 mole of trifluoroacetic acid are used per ester group.

19. A process according to claim 1, wherein the transesterification is carried out at a temperature of at least 70° C.

20. A process according to claim 18, wherein the transesterification is carried out at a temperature in the range from 100° C. to 130° C.

21. A process according to claim 1, further comprising continuously feeding the carboxylic acid and the ketoester compound into the reaction mixture, and removing the ketone formed and any ester which forms.

* * * * *

UNITED STATES PATENT AND TRADEMARK OFFICE
CERTIFICATE OF CORRECTION

PATENT NO.    : 5,481,029
DATED         : January 2, 1996
INVENTOR(S)   : Braun et al.

It is certified that error appears in the above-indentified patent and that said Letters Patent is hereby corrected as shown below:

(Claim 1) Column 8, line 21, ketene should read as ketone.

Signed and Sealed this

Twenty-third Day of April, 1996

Attest:

BRUCE LEHMAN

Attesting Officer

Commissioner of Patents and Trademarks